United States Patent [19]

Wood et al.

[11] 4,255,561

[45] * Mar. 10, 1981

[54] SULFIDE POLYMERS OF POLYOXYALKYLENES

[75] Inventors: Lindley S. Wood, Montclair; David J. Tracy, Lincoln Park; Paritosh M. Chakrabarti, Wayne, all of N.J.

[73] Assignee: GAF Corporation, New York, N.Y.

[*] Notice: The portion of the term of this patent subsequent to Mar. 31, 1998, has been disclaimed.

[21] Appl. No.: 78,709

[22] Filed: Sep. 25, 1979

[51] Int. Cl.³ .............................................. C08G 75/14
[52] U.S. Cl. .................................. 528/388; 427/389; 427/389.9; 428/411; 428/413; 428/480; 428/532; 525/403; 525/404; 525/409; 528/381; 528/419; 528/421; 568/40; 568/50; 568/62
[58] Field of Search ............... 260/DIG. 15, DIG. 17, 260/DIG. 19, 609 R, 609 F; 427/390 B, 389; 428/411, 413, 480, 532; 528/381, 388, 419, 421; 525/403, 404, 409

[56] References Cited

U.S. PATENT DOCUMENTS

| | | | |
|---|---|---|---|
| 3,627,845 | 12/1971 | Hickner et al. | 260/609 F |
| 4,092,293 | 5/1978 | Harns et al. | 260/609 R |

*Primary Examiner*—Melvyn I. Marquis
*Attorney, Agent, or Firm*—James Magee, Jr.; Merilyn J. Mane

[57] ABSTRACT

The sulfide polymers of polyoxyalkylenes having the formula:

$$MS\{-[(AO)_x-(BO)_y-(CO)_z]_n-D-S\}_m M \qquad I.$$

wherein M is alkyl of from 1 to 4 carbon atoms, benzyl, phenyl, hydrogen or an alkali metal or ammonium ion; A, C and D represent lower alkylene of 2 to 4 carbon atoms; B is alkylene of 2 to 8 carbon atoms; y and z are each integers having a value of 0 to 50; x is an integer having a value of from 1 to 50; n is an integer having a value of 1 to 30; and m has a value of from 2 to 10; and intermixtures of said polyoxyalkylene sulfide polymers.

The above polymers have excellent antioxidating properties and are useful as synthetic metal working lubricants, antistatic agents and antioxidants for various other types of applications. They can also be used as crosslinking agents to impart oxidation resistance and static elimination.

20 Claims, No Drawings

SULFIDE POLYMERS OF POLYOXYALKYLENES

The uncrosslinked polymers can be used in blends with alkoxy type resins, particularly epoxy resins, a flexibilizers.

It is an object of this invention to provide novel curing and coating agents. Another object of the invention is to provide novel vulcanizing aids. Still another object is to provide novel polymers which may be crosslinked with siloxanes.

These and other objects and advantages of the present invention will become apparent from the following description and disclosure.

According to the invention, there is provided new and useful sulfide polymers of polyoxyalkylenes having the formula:

$$MS-\{-[(AO)_x-(BO)_y-(CO)_z]_n-D-S\}_m-M \qquad \text{I.}$$

wherein M is alkyl of from 1 to 4 carbon atoms, a benzyl radical, a phenyl radical, hydrogen or alkali metal or ammonium ion; A, C and D represent lower alkylene of 2 to 4 carbon atoms; B is alkylene of 2 to 8 carbon atoms; y and z are each integers having a value of 0 to 50; x is an integer having a value of from 1 to 50; n is an integer having a value of from 1 to 30; and m has a value of 2 to 10. Of these compounds, those wherein x, y and z, taken together, average 6 to 60; A, C and D are the same and are ethylene or isopropylene; and m has an averaged value of 2 to 8 are preferred. Of this preferred group, those most desirable are the compounds wherein y and z are 0; x is an integer between 6 and 25 and D and A are the same alkylene radical. However, it is to be understood that the value of x, y and z, as well as the radicals A, B, C and D in the above compounds and their mixtures, can be varied considerably in accordance with the needs of the particular application in which the product is to be employed.

Examples of sulfide polymers of polyoxyalkylenes within the preferred groups of compounds include those having the generic formulae:

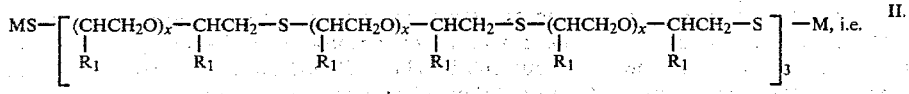

a trimer where the averaged value of x is 20 to about 35 and $R_1$ is hydrogen or methyl;

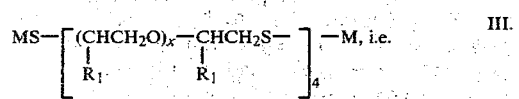

a tetramer where the averaged value of x is about 8 to about 20 and $R_1$ is hydrogen or methyl;

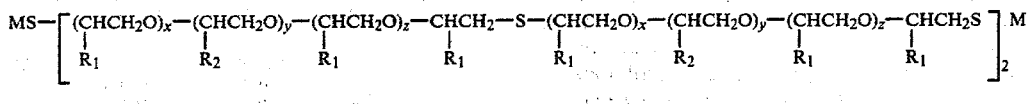

e.g. a dimer wherein $R_1$ and $R_2$ are hydrogen or methyl and $R_2$ is other than $R_1$ and each of x, y and z have a value of 20 to 30;

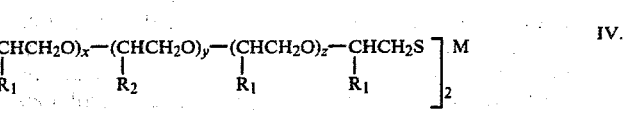

i.e. the dimer wherein $R_1$ and $R_2$ are different and are H or methyl and the averaged values of x, y and z are 2 to 22;

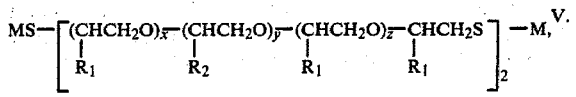

e.g. a dimer where x and z have an averaged value of 20 to 40; $R_1$ is hydrogen or methyl and B is alkylene of 4 to 8 carbon atoms; and

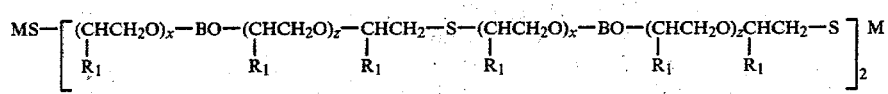

the tetramer wherein $R_1$ is hydrogen or methyl, B is alkylene of 4 to 8 carbon atoms and x and z have an average value of 2 to 22.

In general, the present polymers are prepared by reacting a polyoxyalkylene dihalide, having the formula:

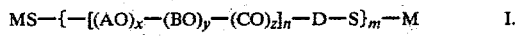

wherein n is 1 to 30; halo is a chlorine, bromine or iodine atom and A, B, C and D as well as x, y and z are as defined in Formula 1, with a sulfur-containing compound selected from the group of alkali metal thiol, ammonium thiol, alkali metal sulfide and ammonium sulfide to provide the thiol and inorganic sulfide terminated polymers; which in turn can be reacted with organic halides such as the benzyl halides, halobenzenes or $C_1$ to $C_4$ alkyl halides, when benzyl, phenyl or $C_1$ to $C_4$ alkyl sulfide terminal group are desired. The reaction is carried out with a high concentration of the reactants, generally in the liquid phase and under superatmospheric pressure conditions.

Although the use of a solvent is not required, in some cases a small amount is beneficial for liquid phase operation. Accordingly, in certain cases, an inert liquid medium in a concentration of between about 5 and 30 weight %, more suitably below 15 weight %, based on total reactants introduced into the reaction zone, may be employed. Suitable solvents are those having a boiling point above reaction temperature and include toluene, xylene, naphthalene, cyclohexanol, cyclohexane, chlorobenzene, octanol, decanol, anisol, creosol, cymene, isobutanol, N-methyl pyrrolidone, pyrrolidone, and the like. Hydrate salts of the sulfur containing reactant, e.g. over a 2 fold excess, may also function as a solvent medium for the reaction.

The mole ratio of polyoxyalkylene dihalide to inorganic sulfur-containing reactant is between about 1:0.8 and about 1:18, preferably between about 1:1 and about 1:2. A high concentration of reactants, e.g. not more than 30 weight % dilution in the reaction zone, is employed.

If desired, the present polymerization can be carried out in the presence of other monomers or polymers, such as a siloxane, an epoxide, or a polyester, to provide the corresponding block copolymers or crosslinked polymers.

The present polymerization reaction is effected at a temperature of between about 70° C. and about 180° C., under from about 30 to about 5,000 psi, and is completed in a period of from about 15 to about 35 hours; preferably the reaction is carried out between about 90° C. and about 160° C., under from about 100 to about 2,000 psi, and is completed within about 25 hours, depending upon the degree of polymerization desired and the molecular weight of the polymeric reactant. The closed system operation of the present invention provides better temperature control, reduced oxidation side reactions and promotes the polymerization of high molecular weight dihalide reactants. The polymeric products of the present process can be obtained in a purity up to 98%, when a solvent is omitted. However, the solvents, when used, can be easily removed by distillation, evaporation or by any other convenient method.

Alternatively, the present reaction can be effected by polymerizing the thiol or inorganic salt thiols of the polyoxyalkylene products of my copending application, Ser. No. 078,708, filed concurrently herewith, the entire disclosure of which is incorporated herein by reference. Polymerization of these thiols or salts of polyoxyalkylenes is initiated by contacting said compounds and inorganic sulfur containing reactant of the present reaction under a pressure in excess of 20 psi with a high concentration of reactants in the reaction zone and at reaction temperature in the absence or in the presence of a catalyst, e.g. a basic catalyst employed in a concentration of between about 0.05 and about 1.5% by weight, based on the polyoxyalkylene salt or thiol. The higher pressurization aids in promoting reaction of more difficultly polymerizable species.

The polyoxyalkylene dihalides and their intermixtures employed in the present invention are readily obtained by reacting the corresponding polyalkylene glycols with a molar excess of thionyl halide at moderate temperatures, e.g. between about 20° C. and about 125° C. under atmospheric pressure for a period of at least 10 hours. The reaction is described in more detail in Belgian Pat. No. 554, 506 filed Jan. 25, 1957 and a general discussion of the glycols is presented in Kirk-Othmer's Encyclopedia of Chemical Technology, second edition, volume 10, page 659. Suitable mixed glycols are commercially marketed, e.g. the PLURONIC$^R$ Polyols, supplied by Wyandotte Chemicals Corporation of which the polyols P104, F108, L43, 25R2, P85 and F127 are particularly useful. Other suitable polyols are listed in Table I.

TABLE I
SUITABLE PLURONIC POLYOLS

| FORM* | PLURONIC GRADE | AVERAGE MOLECULAR WEIGHT | FLASH POINT (COC° F.) | REFRACTIVE INDEX 25° C. |
|---|---|---|---|---|
| L | 10R5 | 1970 | >450 | 1.4587 |
| F | 10R8 | 5000 | >450 | — |
| L | 17R1 | 1950 | >450 | 1.4516 |
| L | 17R2 | 2100 | >450 | 1.4535 |
| L | 17R4 | 2700 | >450 | 1.4572 |
| F | 17R8 | 7500 | >450 | — |
| L | 25R1 | 2800 | >450 | 1.4521 |
| L | 25R2 | 3120 | >450 | 1.4541 |
| L | 25R4 | 3800 | >450 | 1.4574 |
| P | 25R5 | 4500 | >450 | — |
| F | 25R8 | 9000 | >450 | — |
| L | 31R1 | 3200 | >450 | 1.4522 |
| L | 31R2 | 3400 | >450 | 1.4542 |
| P | 31R4 | 4300 | — | — |
| | L31 | 1100 | 37 | — |
| | L35 | 1900 | 77 | — |
| | F38 | 5000 | >100 | 45 |
| | L42 | 1630 | 37 | — |
| | L43 | 1850 | 42 | — |
| | L44 | 2200 | 65 | — |
| | L61 | 2000 | 24 | — |
| | L62 | 2500 | 32 | — |
| | L62LF | 2450 | 28 | — |
| | L62D | 2450 | 35 | — |
| | L63 | 2650 | 34 | — |
| | L64 | 2900 | 58 | — |
| | P65 | 3500 | 82 | 29.5 |
| | F68 | 8350 | >100 | 50 |
| | F68LF | 7700 | 32 | 47 |
| | L72 | 2850 | 25 | — |
| | P75 | 4150 | 82 | 34 |
| | F77 | 6500 | >100 | 48 |
| | L81 | 2750 | 20 | — |
| | P84 | 4200 | 74 | 34 |
| | P85 | 4600 | 85 | 40 |
| | P87 | 7850 | >100 | 49 |
| | F88 | 10,800 | >100 | — |
| | F92 | 3500 | 26 | — |
| | P94 | 4600 | 76 | 38 |
| | F98 | 13,500 | >100 | 56 |
| | L101 | 3800 | 15 | — |
| | P103 | 4900 | 86 | 30 |
| | P104 | 5800 | 81 | 37.5 |
| | P105 | 6350 | 91 | 42 |
| | F108 | 15,500 | >100 | 57 |
| | L121 | 4500 | 14 | — |
| | L122 | 4900 | 19 | — |
| | F123 | 5650 | 90 | — |
| | P127 | 11,500 | >100 | 56 |

*L - LIQUID
P - PASTE
F - FLAKABLE SOLID

As stated above, the sulfide polymers of the present invention are useful as coating modifiers, vulcanization agents, polymer modifiers and blending agents. In addition, the products of the present invention are antistatic agents which can be impregnated into hydrophobic fabrics, either chemically or mechanically, by padding about 100 to about 50,000 parts per million parts of fabric followed by drying and curing. The material so finished shows a marked decrease in electrical resistivity, such that the electrostatic conductivity of a specific area of fabric is significantly increased. Also, the polymeric products of the present invention can be intimately incorporated into the hydrophobic polymer by conducting the polymerization of the hydrophobic monomer, or monomer and comonomer, in the presence of between about 0.05 and about 20 weight % of instant sulfide polymer to form the interpolymer containing dispersed units of the sulfide polymer in the hydrophobic polymer and/or copolymer species. These modifications of synthetic fibers improve their launderability and provide filler for better body and hand in fabrics produced from said fibers.

Having generally described the invention, reference is now had to the accompanying examples which illustrate preferred embodiments but which are not to be construed as limiting to the scope of the invention as set forth above and as defined in the accompanying claims. All amounts and proportions recited in the following examples are by weight, unless otherwise indicated.

EXAMPLE 1

A. Into a one gallon, jacketed, stainless steel pressure kettle equipped with a mechanical stirrer, is added 179 grams of aqueous 40% sodium thiol. To the resulting mixture is introduced 526 grams of a polyoxyethylene dibromide mixture (PEG 400 dibromide), having the formula:

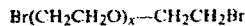

wherein x has an averaged value of 8. The kettle is then sealed and pressurized to about 200 psi and the contents refluxed for 20 hours during which the reaction mixture is constantly stirred. The pressure is then released, water evaporated, and the mixture is gradually cooled to 15°-20° C. over a period of 2 hours, after which sodium bromide precipitate is filtered from the corresponding product mixture of oxyethylene sulfide polymer, having the average molecular weight corresponding to the formula:

$$HS-[-(CH_2CH_2O)_x-CH_2CH_2-S-]_4-H$$

where x has an averaged value of 8. The product is recovered in 90% yield and 98% purity. The sulfur analysis is 9.7%.

B. The above reaction is repeated except that the polyoxyethylene dibromide is replaced with polyoxyethylene diiodide wherein the mole ratio of sodium thiol to polyoxyethylene diiodide salt is 7:1. After 18 hours, the corresponding product mixture of oxyethylene sulfide polymer having the formula:

$$HS-[(CH_2CH_2O)_8-CH_2CH_2-S-]_6H$$

wherein 8 and 6 are averaged values; is recovered as a viscous liquid in 93% yield and 95% purity. The sulfur analysis is 9.1%. When other polyoxyethylene dihalides, or polyoxypropylene dihalides such as for example those of the above formula wherein x is 10, 12 or 21 are substituted in the above example part A or B, the corresponding oxyalkylene sulfide polymers are obtained in yield above 75% and in a purity of 80% or higher.

EXAMPLE 2

A. Into a one gallon, jacketed, stainless steel pressure kettle equipped with a mechanical stirrer, containing 150 ml of toluene is added the product of Example 1A and ethyl bromide in a mole ratio of 1:3. The kettle is then sealed and the contents refluxed for 15 hours during which the reaction mixture is constantly stirred and autogenous pressure develops (20–30 psi). The mixture is then gradually cooled to room temperture over a period of 2 hours. Hydrogen bromide is vented from the reaction mixture and the corresponding product mixture, having the formula:

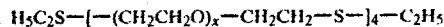

where x has an averaged value of 8, is recovered by filtration in 90% yield and 90% purity.

B. Part A of this example is repeated except that bromobenzene is substituted for ethyl bromide. The corresponding product mixture of oxyethylene sulfide polymer having the formula:

is recovered in 85% yield and purity.

C. When benzyl bromide is substituted for ethyl bromide in part A of this example, the corresponding product mixture having the formula:

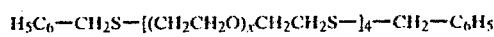

is obtained in 85% yield and purity.

EXAMPLE 3

A. Into a one gallon, jacketed, stainless steel pressure kettle equipped with a mechanical stirrer, containing 225 grams of sodium sulfide; is introduced 1310 grams of a polyoxyethylene dichloride mixture (PEG 400 dichloride), having the formula:

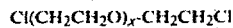

wherein x has an averaged value of 8. The kettle is then sealed and pressurized to 200 psi and the contents refluxed for 20 hours during which the reaction mixture is constantly stirred. After removal of water by release of pressure, the mixture is gradually cooled to 15°-20° C. over a period of 2 hours, after which unreacted sodium sulfide and sodium chloride precipitate is filtered from the corresponding product mixture of oxyethylene sulfide polymer, having an average molecular weight corresponding to the formula:

$$NaS-[-(CH_2CH_2O)_x-CH_2CH_2-S]_4-Na$$

where x and n both have an averaged value of 8. The product is recovered in 95% yield and 98% purity. The sulfur analysis is 9.4%.

B. Part A of this example is repeated except that the polyoxyethylene dichloride is replaced with polyoxypropylene dibromide having the formula:

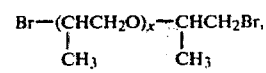

where x has an averaged value of 10 and the dibromide polymer is reacted with sodium sulfide in a mole ratio of 1:1. After 16 hours, the corresponding product mixture of oxyethylene sulfide polymer having the formula:

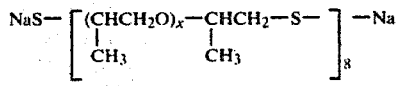

where x has an averaged value of 10, is recovered as a heavy viscous liquid in 85% yield and purity.

EXAMPLE 4

A. Into a one gallon, jacketed, stainless steel pressure kettle equipped with a mechanical stirrer, containing 150 ml of toluene is added the product of Example 3B and methyl bromide in a mole ratio of 1:3. The kettle is then sealed and refluxed with constant stirring for 20 hours. The mixture is then gradually cooled to room temperature over a period of 2 hours, after which sodium bromide is filtered and the solvent is distilled from the corresponding sulfide product mixture of oxypropylene polymer, having the formula:

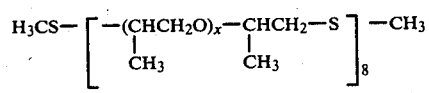

where x has an averaged value of 10. The product is recovered in 90yield and 95% purity.

B. The above reaction is repeated except that chlorobenzene is substituted for methyl bromide and the corresponding sulfide mixture of oxypropylene polymer having the formula:

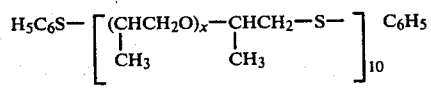

where x has an averaged value of 10, is recovered as a semi-solid in 90% yield and 95% purity.

EXAMPLE 5

A. Into a one gallon, jacketed, stainless steel pressure kettle equipped with a mechanical stirrer, is added 171 grams of 23% aqueous ammonium sulfide solution and 850 grams of a polyoxyethylene polyoxypropylene dihalide having the formula:

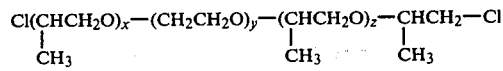

wherein each of x and z has an averaged value of 20 and y has an averaged value of 10. The kettle is then sealed, pressurized to 2,500 psi and the temperature is raised and held at 120° C. for 28 hours during which the reaction mixture is constantly stirred. The pressure is then released, water removed and the reaction gradually cooled to 15°-20° C. over a period of several hours, after which ammonium chloride is filtered from the corresponding product mixture of oxyalkylene sulfide polymer, having the formula:

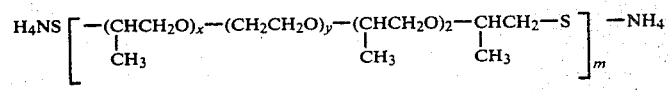

where x, y and z are as defined above and m has an averaged value of 6. The product is recovered in 80% yield and 85% purity. The sulfur analysis is 1.9%.

B. The above reaction is repeated except that 140 grams of potassium sulfide 44% aqueous solution, is substituted for ammonium sulfide and is employed to serve both as reactant and solvent in the process wherein the mole ratio of potassium sulfide to polyoxyalkylene dichloride salt of 1.125:1 is employed. After 16 hours, the corresponding product mixture of oxyalkylene sulfide polymer having the formula:

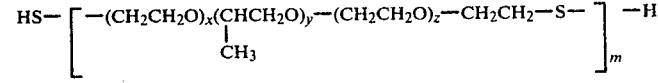

where x, y and z are as defined above in part A and m has an averaged value of 6, is recovered as a plastic semisolid in 85% yield and 90% purity. The sulfur analysis is 1.95%.

EXAMPLE 6

A. Into a one gallon, jacketed, stainless steel pressure kettle equipped with a mechanical stirrer, containing 100 ml of toluene, is added 139 grams of sodium sulfide, 9 hydrate and 620 grams of a polyoxyethylene polyoxypropylene dichloride, having the formula:

$$Cl(CH_2CH_2O)_x-(CHCH_2O)_y-(CH_2CH_2O)_z-CH_2CH_2Cl$$
$$\underset{CH_3}{|}$$

wherein x+z have an averaged value of 12 and y has an averaged value of 10. The kettle is then sealed, pressurized to 2,000 psi and the temperature raised and held at 120° C. for 20 hours during which the reaction mixture is constantly stirred. The pressure is then released, water removed and the mixture is gradually cooled to 15°-20° C. over a period of several hours. The pH of the mixture is adjusted to 6 by addition of glacial acetic acid so as to convert the sodium salt to the free acid and the resulting sodium acetate and sodium chloride precipitate is filtered from the product mixture of oxyalkylene sulfide polymer, having the formula:

$$HS-\left[-(CH_2CH_2O)_x(CHCH_2O)_y-(CH_2CH_2O)_z-CH_2CH_2-S-\right]_m-H$$
$$\phantom{HS-\left[-(CH_2CH_2O)_x\right.}\underset{CH_3}{|}$$

where x, y and z are as defined above and m has an averaged value of 6. The product is recovered in 80% yield and 90% purity. The sulfur analysis is 2.88%.

B. The above reaction is repeated except that toluene is omitted and 78 grams of 40% aqueous sodium thiol (NaSH) is employed to serve both as reactant and solvent in the process wherein the mole ratio of sodium thiol to polyoxyalkylene dichloride salt is 1.125:1. The corresponding product mixture of oxyalkylene sulfide polymer having the formula:

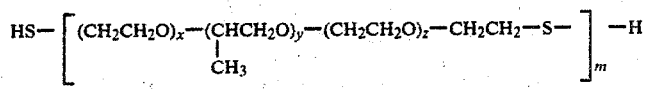

where x, y and z are as defined above in part A of this example and m has an averaged value of 8, is recovered as a plastic semi-solid in 85% yield and 90% purity. The sulfur analysis is 2.78%.

EXMPLE 7

A. Into a one gallon, jacketed, stainless steel pressure kettle equipped with a mechanical stirrer, containing 150 ml of chlorobenzene is added 88 grams of 40% aqueous sodium thiol. To the resulting mixture is introduced 615 grams of a polyoxyethylene oxybutylene dichloride, having the formula:

$$Cl(CH_2CH_2O)_x-CH_2CH_2CH_2CH_2O-(CH_2CH_2O)_z-CH_2CH_2Cl$$

wherein x+z have an averaged value of 24. The kettle is then sealed, pressurized to 3,000 psi and the temperature raised and held at 120° C. for 25 hours during which the reaction mixture is constantly stirred. Pressure is then released, water removed and the mixture is gradually cooled to 15°–20° C. over a period of several hours. The pH is adjusted to 6 with glacial acetic acid and the resulting sodium acetate and sodium chloride precipitate is filtered. The chlorobenzene is steam distilled from the corresponding product mixture of oxyalkylene sulfide polymer, having the formula:

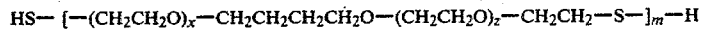

where x and z are as defined above and m has an averaged value of 4. The product is recovered in 80% yield and 90% purity. The sulfur content is analyzed at 3.0%.

B. The above reaction is repeated except that chlorobenzene is omitted and 82 grams of 40% aqueous sodium thiol solution is employed to serve both as reactant and solvent in the process wherein the mole ratio of sodium thiol to polyoxyalkylene dichloride salt is 15:1. After 16 hours, and pH adjustment, the corresponding product mixture of oxyalkylene sulfide polymer having the formula:

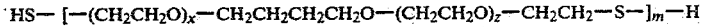

where x, y and z are as defined above in part A and m has an averaged value of 6, is recovered as a plastic semi-solid in 85% yield and 90% purity. The sulfur analysis is 2.82%.

C. Part B of this example is repeated except that polyoxyethylene oxybutylene dichloride is replaced by polyoxypropylene oxyoctylene dichloride having the formula:

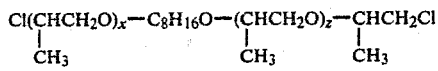

wherein x+z have an averaged value of 12. The resulting product having the formula:

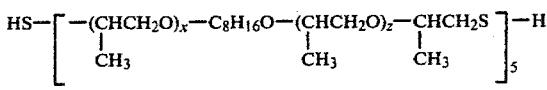

is recovered in 80% yield and 90% purity.

EXAMPLE 8

A. Into a one gallon, jacketed, stainless steel pressure kettle equipped with a mechanical stirrer, containing 150 ml of toluene is added the product of Example 7A and bromobenzene in a mole ratio of 1:3. The kettle is then sealed and the contents refluxed for 20 hours during which the reaction mixture is constantly stirred and autogenous pressure develops. The mixture is then gradually cooled to room temperature over a period of 2 hours, after which chlorobenzene by-product and xylene are hydrogen bromide is vented and toluene is removed by distillation from the corresponding sulfide polymeric mixture having the formula:

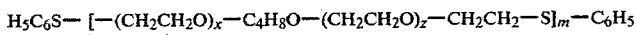

where x and z have an averaged values assigned in example 7A and m has an averaged value of 4. The product is recovered in 80% yield and 90% purity. The sulfur analysis is 2.98%.

B. The above reaction is repeated except that propyl bromide is substituted for bromobenzene in Part A of this example. The corresponding product mixture oxypropylene sulfide polymer having the formula:

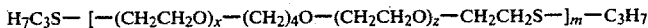

wherein x, y and m are as defined in Example 7A, is recovered as a plastic semi-solid in 85% yield and 90% purity. Sulfur is analyzed at 2.98%.

C. The product of Example 7C and butyliodide, in a mode ratio of 1:3 are added to 200 ml of toluene and refluxed for 15 hours in a sealed kettle while stirring. Hydrogen iodide is vented and the liquid mixture is gradually cooled to room temperature. Toluene is evaporated and the corresponding product mixture:

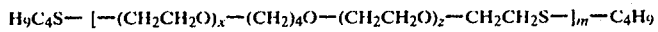

wherein x, z and m are as defined in example 7A, is recovered in 80% yield and 85% purity.

EXAMPLE 9

A. Into a one gallon, jacketed, stainless steel pressure kettle equipped with a mechanical stirrer, containing 150 ml of chlorobenzene is added 34 grams of a 40% aqueous solution of sodium sulfide. To the resulting mixture is introduced 920 grams of a polyoxyethylene polyoxypropylene dichloride of a substantially random 1:1 monomeric structure and having the formula:

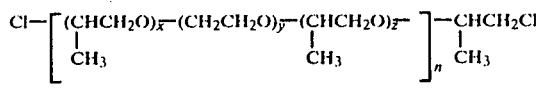

wherein x, y, z and n have an averaged values of 2, 5, 2 and 12 respectively. The kettle is then sealed and temperature raised to 120° C. and pressurized to 5000 psi for 20 hours during which the reaction mixture is constantly stirred. The mixture is then gradually cooled to 15°–20° C. over a period of several hours, and the pH is adjusted to 6 with glacial acetic acid. The resulting sodium acetate/sodium chloride precipitate is filtered and the solvent and water are distilled from the corresponding product mixture of oxyalkylene sulfide polymer, having the formula:

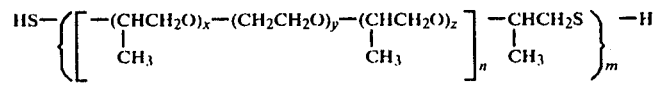

where x, y, z and n have averaged values given above and m has an averaged value of 4. The product is recovered in 80% yield and 90% purity. The sulfur analysis is 0.76%.

B. The above reaction is repeated except that chlorobenzene is omitted and 32.7 grams of 40% aqueous sodium thiol is employed to serve both as reactant and solvent in the process wherein the mole ratio of sodium thiol to polyoxyalkylene dibromide salt is 1.17:1. After 16 hours, the corresponding product mixture of oxyalkylene sulfide polymer having the formula:

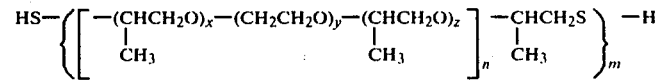

wherein x, y, z and n are as defined in part A of this example and m has an averaged value of 8, is recovered in 85% yield and 90% purity. Sulfur is analyzed at 0.74%.

When other polyoxyethylene halides, or polyoxypropylene halides such as for example those wherein x, y and z are each 10, 12, 21 or 30 and n is 15, 20 or 25, are substituted in the above example art A or B, the corresponding oxyalkylene sulfide polymers are obtained in yield above 75% and in a purity of 80% or higher.

EXAMPLE 10

A. Into a one gallon, jacketed, stainless steel pressure kettle equipped with a mechanical stirrer, containing 150 ml of chlorobenzene is added a 40% aqueous solution of sodium thiol and polyoxyethylene/polyoxypropylene bromide, having the formula:

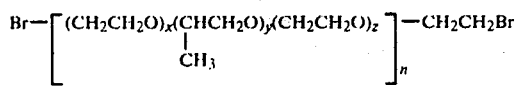

wherein the averaged values of x, y and z are each 25 and the averaged value of n is 20. The mole ratio of thiol to polymer is about 1:1. The kettle is then sealed, pressurized to 1,000 psi and refluxed for 18 hours during which the reaction mixture is constantly stirred. The pressure is then released, water and solvent removed and the mixture is then gradually cooled to 15°–20° C. The pH of the mixture is adjusted to 6 with glacial acetic acid and the resulting sodium acetate/sodium chloride precipitate is filtered from the corresponding product mixture of oxyalkylene thiol polymer having the formula:

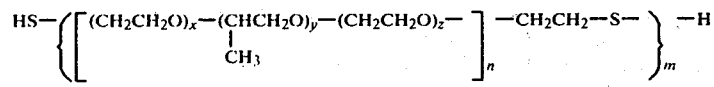

wherein the averaged values of x, y, z and n are as defined above and the averaged value of m is 2. The product is recovered in 80% yield and 90% purity. Sulfur analyzed at 0.83%.

B. The above reaction is repeated except that ammonium sulfide is substituted for sodium thiol. The corresponding product mixture of oxyalkylene polymer having the formula:

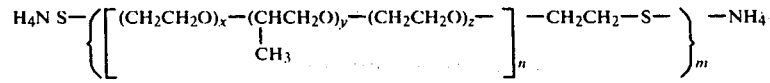

wherein the averaged values of x, y and n are as defined above and the averaged value of m is 6, is recovered in 85% yield and 90% purity. The sulfur analysis is 0.8%.

C. The product of 10B above and methyl bromide in a mole ratio of 1:3 are mixed in 150 ml of toluene and refluxed for 15 hours, the ammonium bromide by-product is filtered and the product:

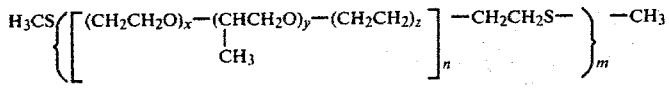

where x, y, z and n are as defined in 10A and m has an averaged value of 6, is recovered in 80% yield and 90% purity.

D. Part A of this example is repeated except that a solvent is omitted; polyoxyethylene dichloride having the formula:

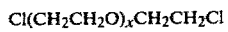

wherein x has an average value of 12, is substituted for the polyoxyethylene/polyoxypropylene dihalide and the reaction is pressurized to only 500 psi. The corresponding product having the formula:

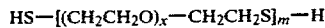

wherein x and m have averaged values of 12 and 6 respectively is recovered in 90% yield and 95% purity.

EXAMPLE 11

A. Into a one gallon, jacketed, stainless steel pressure kettle equipped with a mechanical stirrer, containing 150 ml of chlorobenzene is added 31.5 grams of 40% aqueous sodium thiol. To the resulting mixture is introduced 530 grams of a random 1:1 polyoxyethylene/-polyoxypropylene dichloride, polymer having the formula:

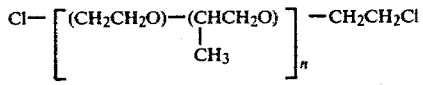

wherein the averaged value of n is 25. The kettle is then sealed, and pressurized to 200 psi and the temperature raised and held at 120° C. for 18 hours during which the reaction mixture is constantly stirred. After depressurizing and removing water and solvent, the mixture is then gradually cooled to 15°–20° C. over a period of several hours. The pH, is adjusted to 6 with glacial acetic acid and the sodium acetate/sodium chloride precipitate is filtered from the corresponding product mixture of oxyalkylene sulfide polymer, having the formula:

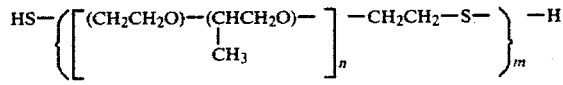

wherein the averaged values of n and m are 25 and 8 respectively. The product is recovered in 80% yield and 90% purity. The sulfur analysis is 1.25%.

B. The above reaction is repeated except that chlorobenzene is omitted and 31.1 grams of 40% aqueous potassium thiol (KSH) is employed in the process wherein the mole ratio of sodium thiol to polyoxyalkylene dichloride salt is 1.11:1. After 15 hours, the pH is adjusted to 6 with glacial acetic acid, the salts removed and water stripped to give the corresponding product mixture of oxyalkylene polymer having the formula:

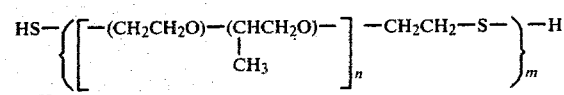

wherein the averaged values of n and m are 25 and 9 respectively, in 85% yield and 90% purity. Sulfur analyzed at 1.21%.

EXAMPLE 12

The products of Examples 1 through 11 are each dissolved in methylene chloride or water to provide 2% solutions. A 1.5×11.5 inch strip of Dacron 56 Taffeta is immersed in each of the solutions for approximately 10 minutes. The impregnated strip is then removed and air dried without curing and tested for electrostatic build-up. Each of the impregnated strips was stroked 50 times against a polyvinyl-chloride fabric surface and then placed on top of an ashtray containing cigarette ashes. There was no ash pick-up on the strip which indicates complete discharge of static electricity.

The products of Examples 1 through 11 are not merely formed as a coating film on the fabric but actually penetrate into the intersticies of the weave and have affinity for the fabric such that the antistatic property has a more lasting effect.

The above results are repeated when strips of nylon, orlon or arnel are substituted for Dacron in the above example.

EXAMPLE 13

Aqueous solutions of each of the products of Examples 1 through 11 (5 grams/liter) are made up in glass flasks. Acrylonitrile monomer is added with stirring to each of the aqueous solutions and a stable emulsion formed upon addition. Polymerization is initiated at 55° C. in the presence of 0.3 gram ammonium persulfate catalyst. The polymerization reaction is effected at 60–70% without agglomeration of the polymerizing particles and polyacrylonitrile is recovered as a particulate solid.

EXAMPLE 14

The following formulation is made up and mixed with an electric beater at a temperature of about 100° C.

Mineral Oil—35 parts
Melted Beeswax—2 parts
The product of Example 1—12 parts
Spermaceti—11 parts
Glycerin—4 parts Water—36 parts The above formulation is allowed to stand for 48 hours. No separation of the resulting homogeneous mixture is evidenced and the creamy product has excellent penetrating properties for use as a moisturizing cream.

It is to be understood that other cosmetic formulations made from other polymeric mixtures wherein the average x, y and z is, for example 10, 12, 16, 24 and higher and the averaged value of m is 2–10; and wherein the polymeric product contains at least two different monomeric units. Such as for example wherein A, C and D are ethylene and B is isopropylene or wherein A, C and D are isopropylene and B is ethylene or wherein A, C and D are ethylene or isopropylene and B is butylene; pentylene, hexylene, heptylene or octylene and many other combinations which are apparent from the foregoing description and disclosure, can be substituted in Examples 12 through 14 and give good results.

What we claim is:

1. A sulfide polymer of polyoxyalkylene having the formula:

$$MS-\{[(AO)_x-(BO)_y-(CO)_z]_n-D-S-\}_m-M$$

where M is alkyl of from 1 to 4 carbon atoms, benzyl, phenyl, hydrogen or an alkali metal or ammonium ion; A, C and D represent lower alkylene of 2 to 4 carbon atoms; B is alkylene of 2 to 8 carbon atoms; y and z are each integers having a value of from 0 to 50; x is an integer having a value of from 1 to 50; n is an integer having a value of 1 to 30; and m has a value of from 2 to 10.

2. The polymer of claim 1 wherein the polymer is a mixture; x, y and z taken together have an average value of 7 to 60; A, C and D are the same and are ethylene or isopropylene, and B is other than A.

3. The polymer of claim 1 wherein y and z are zero and x is an integer having a value between about 2 and 25.

4. The polymer of claim 1 having the formula:

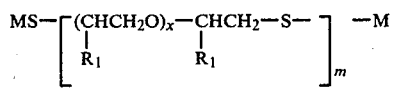

wherein $R_1$ is hydrogen or methyl.

5. The polymer of claim 3 having the formula:

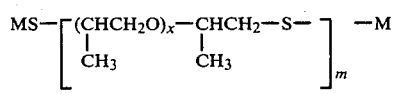

wherein m has an averaged value of from 4 to 8 and x has an averaged value of 2 to 22.

6. The polymer of claim 3 having the formula:

$$MS-[(CH_2CH_2O)_x-CH_2CH_2-S-]_m-M$$

wherein M is alkyl of from 1 to 4 carbon atoms, benzyl or phenyl and m has an averaged value of 4 to 8.

7. The polymer of claim 1 having the formula:

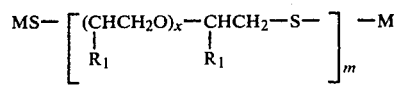

wherein $R_1$ is hydrogen or methyl; M is hydrogen or an ion of sodium, potassium or ammonium; m has an averaged value of 4 to 8 and x has an averaged value of 2 to 22.

8. The polymer of claim 2 having the formula:

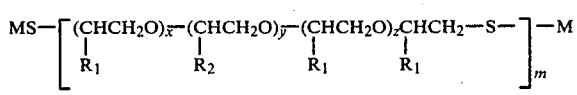

wherein $R_1$ and $R_2$ are each hydrogen or methyl and $R_2$ is different from $R_1$ and m is an integer having an averaged value of 4 to 8.

9. The polymer of claim 2 having the formula:

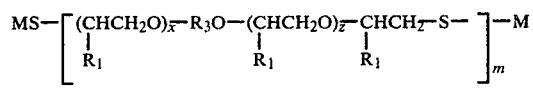

where $R_1$ is hydrogen or methyl and $R_3$ is alkylene having 4 to 8 carbon atoms and the sum of $x+z$ has an averaged value of 12 to 24.

10. The polymer of claim 1 having the formula:

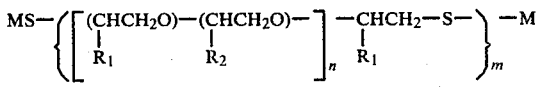

wherein $R_1$ and $R_2$ are each hydrogen or methyl and $R_2$ is other than $R_1$; n is an integer having an averaged value of 4 to 25 and m is an integer having an averaged value of 4 to 9.

11. The polymer of claim 1 having the formula:

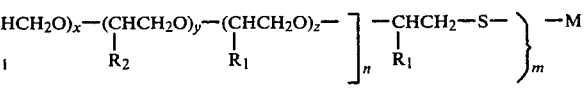

wherein $R_1$ and $R_2$ are hydrogen or methyl and $R_1$ is other than $R_2$; the averaged values of x, y and z are each 2 to 25; and n is 6 to 25.

12. The polymer of claim 1 having the formula:

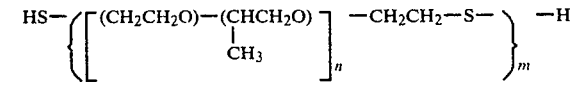

wherein the averaged value of n is 20 to 25.

13. The process of which comprises reacting at an elevated temperature and pressure a concentrated mixture of a sulfur-containing compound selected from the group of ammonium thiol; alkali metal thiol; alkali metal sulfide and ammonium sulfide with at least one dihalide compound having the formula:

$$\text{halo-}[(AO)_x\text{—}(BO)_y\text{—}(CO)_z]_n \text{ D-halo}$$

wherein halo is an atom of chlorine, bromine or iodine; A, C and D represent lower alkylene of 2 to 4 carbon atoms; B is alkylene of 2 to 8 carbon atoms; y and z each represent integers having value of from 0 to 50 and x represents an integer having a value of from 1 to 50; and n an integer from 1 to 30; to produce the product of claim 1.

14. The process of claim 12 wherein the ratio of sulfur-containing compound to said dihalide compound is between about 0.8:1 and about 4:1 and the reaction is carried out over a period of from 15 to 30 hours.

15. The process of claim 12 wherein the reaction is carried out in the presence of not more than 30% by weight, based on the reaction mixture, of an inert organic solvent having a boiling point at least as high as the reaction temperature.

16. The process of claim 13 wherein the dihalide reactant is a mixture of dihalides, having the formula;

$$\text{halo—}(AO)_x\text{D-halo}$$

wherein A and D are the same and are propylene or ethylene and halo and x are as defined in claim 13, is reacted with said sulfur-containing reactant at a temperature of between about 70° C. and about 180° C. under a positive pressure up to about 5,000 psi.

17. The process of claim 13 wherein the polyoxyalkylene dihalide reactant is a mixture of dihalides having the formula:

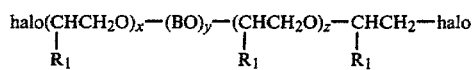

wherein $R_1$ is hydrogen or methyl, B is alkylene of 2 to 8 carbon atoms and (BO) is different from any other monomeric unit in the polymer, x and z are integers from 6 to 20 and y is an integer from 1 to 20, is reacted with said sulfur-containing reactant at a temperature of between about 70° C. and about 180° C. in a closed system under a pressure up to about 5,000 psi.

18. The process of claim 13 wherein between about 5 and about 20 weight % of an inert organic solvent having a boiling point at least as high as the reaction temperture forms the liquid phase of the reaction.

19. The process of claim 13 wherein the product of the process is contacted with an organic halide of the group of alkyl halide of from 1 to 4 carbon atoms; benzoyl halide and phenyl halide and refluxed for a period of from 8 to 20 hours.

20. The process of incorporating between about 0.05 and about 20 weight % of the product of claim 1 with a hydrophobic substance to reduce hydrophobicity.

* * * * *